United States Patent [19]

Ponticello et al.

[11] Patent Number: 5,523,368
[45] Date of Patent: Jun. 4, 1996

[54] WEAKLY BASIC POLYMERIZABLE MONOMERS AND POLYMERS PREPARED THEREFROM

[75] Inventors: Ignazio S. Ponticello, Pittsford; Jerome C. Swartz; Tobias E. Ekeze, both of Rochester, all of N.Y.

[73] Assignee: Johnson & Johnson Clinical Diagnostics, Inc., Rochester, N.Y.

[21] Appl. No.: 435,739

[22] Filed: May 5, 1995

Related U.S. Application Data

[62] Division of Ser. No. 306,341, Sep. 15, 1994, Pat. No. 5,434,270.

[51] Int. Cl.$^6$ .......................... C08F 26/06; C08F 226/02; C08F 220/10
[52] U.S. Cl. .................. 526/258; 526/263; 526/307.2; 526/328.5
[58] Field of Search ................................... 526/258, 263, 526/307.2, 328.5

[56] References Cited

U.S. PATENT DOCUMENTS 4,766,052  8/1988  Nakamura et al. .................... 526/258

*Primary Examiner*—Joseph L. Schofer
*Assistant Examiner*—Wu C. Cheng
*Attorney, Agent, or Firm*—John W. Wallen, III

[57] ABSTRACT

Weakly basic ethylenically unsaturated polymerizable monomers and polymers have been prepared. The monomers are represented by the structure (I):

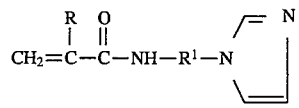

wherein R is hydrogen or methyl, and $R^1$ is alkylene of 1 to 3 carbon atoms. The resulting polymers are water-soluble and cationic at acidic pH, but water-insoluble and neutral in charge at basic pH. The polymers are useful for precipitating nucleic acids.

8 Claims, No Drawings

WEAKLY BASIC POLYMERIZABLE MONOMERS AND POLYMERS PREPARED THEREFROM

This is a division, of application Ser. No. 08/306,341, filed Sep. 15, 1994, which is now U.S. Pat. No. 5,434,270.

RELATED APPLICATION

Reference is made to copending and commonly assigned U.S. application Ser. No. 08/306,870, filed on even date herewith by Backus et al and entitled "Methods for Capture and Selective Release of Nucleic Acids Using Weakly Basic Polymer and Amplification of Same".

1. Field of the Invention

This invention relates to novel ethylenically unsaturated polymerizable monomers and to polymers prepared therefrom. Such polymers have a variety of uses, including their use as nucleic acid capture agents prior to diagnostic methods, as described in more detail in U.S. application Ser. No. 08/306,870 of Backus et al, noted above.

2. Background of the Invention

There is a continuing need in various research and industrial arts for ethylenically unsaturated polymerizable monomers which can be polymerized into useful polymers. For example, in the photographic arts, there is a need for polymers in various layers of photographic elements to provide certain properties. In addition, various analytical elements, such as those sold commercially under the trademark EKTACHEM™ analytical slides, require various polymers in layers as binders, barriers and mordants.

Moreover, there is a continuing need in the field of molecular biology and related diagnostics art for rapid and accurate determinations of nucleic acids which have been extracted from cells or virions. Such nucleic acids can be indicative of the presence of infectious agents or cancerous conditions, or be used for identification of genetic traits. A wide variety of diagnostic methods have been developed in recent years to achieve these purposes.

Isolation of the nucleic acids prior to analysis is usually essential. One major limitation of current analytical methods is the inability to efficiently isolate and concentrate the target nucleic acid in a time and cost efficient manner. Current methods for isolation usually involve phenol/chloroform extractions, ethanol precipitation, binding to various matrices with subsequent elution. These methods are labor intensive, tedious and may involve expensive or environmentally harmful materials. Thus, they are not practical for routine use in analytical laboratories or doctors' offices.

Capture of nucleic acids has been achieved using polyethyleneimine to precipitate nucleic acids, followed by release from the precipitate using a fluorinated phosphate ester. While this technique can be used with some success, it requires the use of two separate reagents in carefully controlled amounts. An improvement has been sought.

A publication by Handel et al, *Macromolecules* 20, pages 264–267 (1987) describes a polymerizable monomer, N-(1,1-dimethyl-3-imidazolylpropyl)acrylamide, and a homopolymer thereof. The effects of the long side chain linking the imidazolyl group were studied. No use is described.

SUMMARY OF THE INVENTION

The noted copending U.S. application Ser. No. 08/306,870 of Backus et al describes a group of weakly basic polymers which provide such an improvement. Within that group of polymers is a smaller group of materials which are the subject of this invention.

Thus, this invention provides a compound of the structure (I):

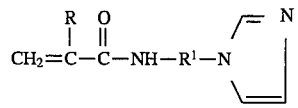

wherein R is hydrogen or methyl, and $R^1$ is alkylene of 1 to 3 carbon atoms, or an acid addition salt of the compounds.

Further, a polymer which is weakly basic at acidic pH comprises recurring units derived by addition polymerization from a weakly basic ethylenically unsaturated polymerizable monomer having structure (I) noted above.

This invention also provides a copolymer which is weakly basic and water-soluble at acidic pH, the copolymer comprising recurring units derived by addition polymerization from:

(a) about 10 to about 99.9 weight percent of a weakly basic ethylenically unsaturated polymerizable monomer having structure (I) noted above, (b) from about 0.1 to about 90 weight percent of a nonionic, hydrophilic ethylenically unsaturated polymerizable monomer, and (c) 0 to about 80 weight percent of a nonionic, hydrophobic ethylenically unsaturated polymerizable monomer.

The polymers of this invention can be used to advantage to capture nucleic acids by forming a precipitate at acidic pH, for subsequent release and detection at basic pH. The particular monomers of this invention can be copolymerized with other acrylates or acrylamides more readily and more homogeneously than similar monomers, such as N-vinylimidazole or 2-methyl-N-vinylimidazole, can be so copolymerized. These monomers are also hydrolytically stable at both high and low pH.

The polymers of this invention can also be used as mordants to bind proteins or any kind, bacteriosides, or as pH barrier films in various elements.

The polymers are weakly basic, meaning that they are cationic at acidic pH, but exist as a free base at basic pH. In addition, they are water-soluble at acidic pH, and water-insoluble at basic pH.

DETAILED DESCRIPTION OF THE INVENTION

The monomers of this invention can be used to prepare either homopolymers or copolymers. These monomers are defined by the structure (I):

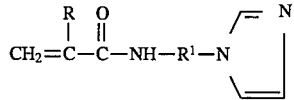

wherein R is hydrogen or methyl. Preferably, R is methyl. In addition, $R^1$ is branched or linear alkylene of 1 to 3 carbon atoms (such as methylene, ethylene, trimethylene or propylene). Preferably, $R^1$ is alkylene of 2 or 3 carbon atoms. More preferably, $R^1$ is trimethylene. Acid addition salts of these compounds can also be prepared.

Particularly useful monomers having structure (I) include, but are not limited to, N-(3-imidazolylpropyl)methacrylamide, N-(2-imidazolylethyl)methacrylamide, N-(3-imidazolylpropyl)acrylamide, and N-(imidazolylmethyl)acrylamide, and their acid addition salts. The first compound is most preferred.

The monomers of structure (I) can also be provided and used in the form of their acid addition salts (such as the hydrochloride).

Compounds of this invention represented by structure (I) can be prepared generally by condensation of a 1-(aminoalkyl)imidazole with a (meth)acryloyl chloride using appropriate conditions which would be readily apparent to one skilled in polymer chemistry. A representative preparation is provided in Example 1 below.

While the monomers described above can be polymerized to form homopolymers, preferably they are copolymerized with one or more other ethylenically unsaturated polymerizable monomers by addition polymerization.

The resulting polymers are weakly basic and water-soluble at acidic pH, and comprise recurring units derived by addition polymerization from:

(a) about 10 to about 99.9 weight percent of one or more monomers defined by structure (I) identified above, (b) from about 0.1 to about 90 weight percent of one or more nonionic, hydrophilic ethylenically unsaturated polymerizable monomers, and (c) 0 to about 80 weight percent of one or more nonionic, hydrophobic ethylenically unsaturated polymerizable monomers.

The monomers identified in (b) are best defined as those having polar (that is, hydrophilic) groups such as hydroxy, primary, secondary or tertiary amine (including cyclic amine groups such as imidazolyl and pyridyl), amide, sulfonamide and polyoxyethylene groups, which will form water-soluble homopolymers when homopolymerized. They can include, but are not limited to, acrylamide, N-vinylimidazole, 2-hydroxyethyl acrylate, 2,3-dihydroxypropyl acrylate, 2,3-dihydroxypropyl methacrylate, 3-(N,N-dimethylamino)propyl acrylate hydrochloride, 2-aminoethyl methacrylate hydrochloride, poly(ethyleneoxy)ethyl methacrylate (having 2 to 10 ethyleneoxy groups) and N,N-dimethyl acrylamide. Acrylamide is preferred.

Monomers for (c) are best defined as those which, when homopolymerized, form water-insoluble (hydrophobic) homopolymers. Generally, such monomers are vinyl aromatics or have alkyl ester groups. Representative monomers identified above in (c) include, but are not limited to, styrene, vinyltoluene, methyl acrylate, ethyl acrylate, butyl acrylate and others which would be readily apparent to one skilled in the art.

Preferably, the copolymers are composed of recurring units derived from about 20 to about 99.9 weight percent of (a), from about 0.1 to about 80 weight percent of (b), and from 0 to about 50 weight percent of (c).

As used herein in defining amounts of monomers, the modifier "about" refers to a maximum variation of ±5%.

Any of the monomers described above can be copolymerized using conventional procedures to form a copolymer as long as the resulting copolymer is cationic and water-soluble at acidic pH, and neutral in charge at basic pH.

The homopolymers and copolymers of this invention are prepared using standard solution polymerization methods which are well known in the art, although there are certain preferred conditions which are illustrated in Examples 2–4 below.

Solution polymerization generally involves dissolving the monomers in a suitable solvent (including water or various water-miscible organic solvents) and polymerizing in the presence of a suitable water-soluble catalyst. The resulting polymer is water-soluble, so it is precipitated using a solvent such as acetone, purified and redissolved in water for future use.

Representative polymers of this invention include, but are not limited to, poly[N-(3-imidazolylpropyl)methacrylamide hydrochloride], poly[N-(3-imidazolylpropyl)methacrylamide hydrochloride-co-acrylamide] (90:10 weight ratio), poly[N-(3-imidazolylpropyl)methacrylamide hydrochloride-co-2-hydroxyethyl methacrylate] (20:80 weight ratio), and poly [N-(3-imidazolylpropyl)methacrylamide hydrochloride-co-acrylamide-co-2-hydroxyethyl methacrylate] (30:40:30 weight ratio).

The following examples are included to illustrate the practice of this invention, and are not meant to be limiting in any way. All percentages are by weight unless otherwise noted.

EXAMPLE 1

Preparation of N-(3Imidazolylpropyl)methacrylamide

This procedure shows the preparation of the most preferred monomer of this invention, but the preparation is representative of how other monomers within the scope of this invention could readily be prepared.

A solvent mixture was prepared by mixing water (100 ml) containing sodium hydroxide (12.8 g, 0.32 mole) and dichloromethane (200 ml) containing 1-(3-aminopropyl)imidazole (37.5 g, 0.3 mole), and cooled in an ice bath. To this cooled mixture was added all at once, methacryloyl chloride (34.8 g, 0.3 mole) in dichloromethane (100 ml) with vigorous stirring under a nitrogen atmosphere. Heat was evolved with the temperature of the mixture rising to about 60° C., and the mixture was vigorously stirred for another 10 minutes, and then the organic layer was allowed to separate. The water layer was extracted twice with dichloromethane (100 ml each time). The combined organic solution (the organic solvent layer and extracts) was washed with saturated sodium chloride (100 ml), dried over anhydrous sodium sulfate, filtered, and the solvent was removed. The residue was dissolved in chloroform (50 ml), followed by the addition of ethyl ether (50 ml) to the cloud point.

The resulting reaction product crystallized at about 0° C., and was filtered to give a white solid having a melting point of 45°–46° C. The yield was 70%.

Analytical data included: m/e (M-193),

1H NMR (DMSO d6 ) 1.8 (m, 2H, C—$CH_2$—C,$CH_3$), 3.02 (m,2H, N—$CH_2$), 3.95 (t,2H, im-$CH_2$), 5.25 and 5.6 (AB,2H,vinyl-$CH_2$), 6.82 and 7.15 (AB,2H,4,5-H of im), 7.6 (s,1H,2-H of im), 7.95 (m, 1H,NH).

EXAMPLE 2

Preparation of Homopolymer

A preferred homopolymer of this invention was prepared by adding 2,2'-azobis (2-methylpropionitrile) (300 mg) to a solution of N-(3-imidazolylpropyl)methacrylamide (12.5 g, 0.065 mole) in water (90 ml) and isopropanol (10 ml), maintained under a nitrogen atmosphere. The resulting solution was heated, while being stirred, to 65°–70° C. in a water bath for 3 hours. After about 1.5 hours of that time, concentrated HCl (3 ml) was added, and the stirring was continued under nitrogen for the remaining time. The solution was then concentrated on a rotary evaporator to about 25 ml, and the resulting polymer product was precipitated in acetone (over 4 liters), filtered and dissolved in deionized water (80 ml). The solution contained 12% solids. Yield of 75%.

EXAMPLE 3

Preparation of Copolymer poly[N-(3-imidazolylpropyl)methacrylamide hydrochloride-co-acrylamide] (90:10 weight ratio) was prepared by adding 2,2'-azobis(2-methylpropionitrile) (400 mg) to a solution of N-(3-imidazolylpropyl)methacrylamide (18 g, 0.09 mole) and acrylamide (2 g, 0.028 mole) in deionized water (120 ml) and isopropanol (15 ml), maintained under a nitrogen atmosphere. The solution was heated to 65°–70° C. with stirring for 4 hours, followed by addition of dilute HCl to lower the pH to about 2. Stirring and heating were continued for another hour, and the solution was then allowed to reach room temperature overnight.

The solution was concentrated to about 75 ml using a rotary evaporator, and the resulting polymer was precipitated in acetone (about 4 liters), filtered and dissolved in deionized water (150 ml). Further concentration to about 125 ml was carried out to remove residual acetone. The polymer was present at 15.5% solids. Yield of 100%.

EXAMPLE 4

Preparation of Second Copolymer

Poly [N-(3-imidazolylpropyl)methacrylamide hydrochloride-co-2-hydroxyethyl methacrylate] (20:80 weight ratio) was prepared by adding 2,2'-azobis(2-methylpropionitrile) (300 mg) to a solution of N-(3-imidazolylpropyl)methacrylamide (4 g, 0.02 mole) and 2-hydroxyethyl methacrylate (16 g, 0.12 mole) in deionized water (180 ml), concentrated HCl (2 ml) and ethanol (20 ml), maintained under a nitrogen atmosphere. The solution was heated to 65°–70° C. with stirring for 5 hours, then allowed to reach room temperature overnight.

The polymer was precipitated in acetone (about 4 liters), filtered and dissolved in deionized water (400 ml). Concentration to about 350 ml was carried out on a rotary evaporator to remove residual acetone. The polymer was present at 5.3%. Yield of 92%.

The invention has been described in detail with particular reference to preferred embodiments thereof, but it will be understood that variations and modifications can be effected within the spirit and scope of the invention.

We claim:

1. A polymer which is weakly basic at acidic pH, said polymer comprising recurring units derived by addition polymerization of a weakly basic ethylenically unsaturated polymerizable monomer of the structure (I):

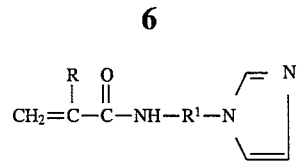

wherein R is hydrogen or methyl, and $R^1$ is alkylene of 1 to 3 carbon atoms, or an acid addition salt of said monomer, wherein said polymer is a homopolymer of said monomer.

2. The polymer of claim 1 wherein R is methyl and $R^1$ is alkylene of 2 or 3 carbon atoms.

3. The polymer of claim 1 wherein said weakly basic monomer is N-(3-imidazolylpropyl)-methacrylamide.

4. A polymer which is weakly basic and water soluble at acidic pH, said polymer comprising recurring units derived by addition polymerization from:

(a) about 10 to about 99.9 weight percent of a weakly basic ethylenically unsaturated polymerizable monomer of the structure (I):

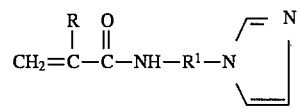

wherein R is hydrogen or methyl, and $R^1$ is alkylene of 1 to 3 carbon atoms, or an acid addition salt of said compound, (b) from about 0.1 to about 80 weight percent of a nonionic, hydrophilic, ethylenically unsaturated polymerizable monomer (b) from about 0.1 to about 80 weight percent of a nonionic, hydrophilic, ethylenically unsaturated polymerizable monomer selected from the group consisting of acrylamide, 2-hydroxyethyl acrylate, 2,3-dihydroxypropyl acrylate, 2,3-dihydroxypropyl methacrylate, N,N-dimethyl acrylamide, poly(ethyleneoxy) ethyl methacrylate having 2 to 10 ethyleneoxy groups, ethyl methacrylate and 2-hydroxyethylmethacrylate.

5. The polymer of claim 4 wherein R is methyl and $R^1$ is alkylene of 2 or 3 carbon atoms.

6. The polymer of claim 4 wherein monomer (a) is N-(2-imidazolylethyl)methacrylamide, N-(3-imidazolylpropyl)acrylamide, N-(imidazolylmethyl)acrylamide or N-(3-imidazolylpropyl)methacrylamide.

7. The polymer of claim 4 wherein monomer (c) is a vinyl aromatic or acrylic ester.

8. The polymer of claim 4 which is poly[N-(3-imidazolylpropyl)methacrylamide hydrochloride], poly[N-(3-imidazolylpropyl)methacrylamide hydrochloride-co-acrylamide] or poly[N-(3-imidazolylpropyl)methacrylamide hydrochloride-co-2-hydroxyethyl methacrylate].

\* \* \* \* \*